US010758281B2

(12) United States Patent
Hansson

(10) Patent No.: US 10,758,281 B2
(45) Date of Patent: Sep. 1, 2020

(54) TARGETING DEVICE AND METHOD

(71) Applicant: SWEMAC INNOVATION AB, Linköping (SE)

(72) Inventor: Henrik Hansson, Vreta Kloster (SE)

(73) Assignee: SWEMAC INNOVATION AB, Linkoping (SE)

(*) Notice: Subject to any disclaimer, the term of this patent is extended or adjusted under 35 U.S.C. 154(b) by 195 days.

(21) Appl. No.: 15/116,240

(22) PCT Filed: Feb. 12, 2014

(86) PCT No.: PCT/SE2014/050171
§ 371 (c)(1),
(2) Date: Aug. 3, 2016

(87) PCT Pub. No.: WO2015/122807
PCT Pub. Date: Aug. 20, 2015

(65) Prior Publication Data
US 2017/0007303 A1 Jan. 12, 2017

(51) Int. Cl.
A61B 17/74 (2006.01)
A61B 17/17 (2006.01)
(Continued)

(52) U.S. Cl.
CPC ........ A61B 17/744 (2013.01); A61B 17/1717 (2013.01); A61B 17/1721 (2013.01);
(Continued)

(58) Field of Classification Search
CPC .................. A61B 17/1721; A61B 17/1725
See application file for complete search history.

(56) References Cited

U.S. PATENT DOCUMENTS 4,465,065 A * 8/1984 Gotfried ............ A61B 17/1721
606/65
4,733,654 A * 3/1988 Marino .............. A61B 17/1721
606/64
(Continued)

FOREIGN PATENT DOCUMENTS

EP 1455662 9/2004
EP 1759643 3/2007
(Continued)

OTHER PUBLICATIONS

Smith & Nephew, Trigen Intertan Intertrochanteric Antegrade Nail, Surgical Technique (2012) 48 pages (Year: 2012).*

Primary Examiner — Jacqueline T Johanas
(74) Attorney, Agent, or Firm — Tarolli, Sundheim, Covell & Tummino LLP

(57) ABSTRACT

The present invention relates to a method for fixing an intramedullary cavity nail for the treatment of unstable trochanteric fractures and to a targeting device for use in performing the steps of said method. According to the method, a recess (16) for a femur neck screw (8) for fixing the cavity nail (2) is provided in at least the lateral cortex of the femoral shaft (FS) in close distal proximity to a hole (9) for the femur neck screw such that bone fragment(s) located distally of the fracture and bone fragment(s) located proximally of the fracture relatively seen can be displaced towards each other. A targeting head (5) of the targeting device (1) is configured with a targeting bore (14) which is alignable with a point on the femoral shaft (FS) in close distal proximity to the hole (9) for the femur neck screw (8) for use in providing at said point, said recess (16) for the femur neck screw.

16 Claims, 14 Drawing Sheets

(51) Int. Cl.
*A61B 17/72* (2006.01)
*A61B 17/92* (2006.01)
*A61B 17/90* (2006.01)

(52) U.S. Cl.
CPC ........ *A61B 17/1725* (2013.01); *A61B 17/725* (2013.01); *A61B 17/7225* (2013.01); *A61B 17/921* (2013.01); *A61B 2017/90* (2013.01)

(56) References Cited

U.S. PATENT DOCUMENTS

| | | | | |
|---|---|---|---|---|
| 4,846,162 A * | 7/1989 | Moehring | .......... | A61B 17/1725 606/67 |
| 5,334,192 A * | 8/1994 | Behrens | ............. | A61B 17/1721 606/102 |
| 5,429,641 A * | 7/1995 | Gotfried | ............ | A61B 17/1721 411/383 |
| 5,766,174 A * | 6/1998 | Perry | ................. | A61B 17/1725 606/62 |
| 5,935,127 A * | 8/1999 | Border | ............... | A61B 17/1721 606/281 |
| 6,106,528 A * | 8/2000 | Durham | ............ | A61B 17/1707 606/62 |
| 6,126,661 A * | 10/2000 | Faccioli | ................. | A61B 17/72 606/64 |
| 7,077,847 B2 | 7/2006 | Pusnik et al. | | |
| 7,311,710 B2 * | 12/2007 | Zander | ............... | A61B 17/1721 606/53 |
| 8,241,286 B2 * | 8/2012 | Metzinger | .......... | A61B 17/1703 606/104 |
| D684,690 S * | 6/2013 | Senger | ............... | A61B 17/1721 D24/140 |
| D684,691 S * | 6/2013 | Senger | ........................ | D24/140 |
| 8,591,517 B2 * | 11/2013 | Metzinger | .......... | A61B 17/1725 606/102 |
| 8,628,531 B2 * | 1/2014 | Ritchey | .............. | A61B 17/1725 606/282 |
| 8,734,448 B2 * | 5/2014 | Thakkar | ............. | A61B 17/1721 606/62 |
| 9,668,791 B2 * | 6/2017 | Khong | ................. | A61B 17/164 |
| 2003/0073999 A1 * | 4/2003 | Putnam | ............. | A61B 17/7291 606/62 |
| 2003/0220651 A1 * | 11/2003 | Pusnik | .............. | A61B 17/1725 606/98 |
| 2005/0096656 A1 * | 5/2005 | Behrens | ............. | A61B 17/1721 606/64 |
| 2007/0219636 A1 * | 9/2007 | Thakkar | ............. | A61B 17/1721 623/18.11 |
| 2008/0119856 A1 * | 5/2008 | Gotfried | ............ | A61B 17/7225 606/67 |
| 2008/0281326 A1 * | 11/2008 | Watanabe | ............ | A61B 17/164 606/62 |
| 2009/0048598 A1 * | 2/2009 | Ritchey | .............. | A61B 17/1725 606/57 |
| 2009/0149861 A1 * | 6/2009 | Brodsky | ............ | A61B 17/1725 606/96 |
| 2009/0299375 A1 * | 12/2009 | Wack | .................. | A61B 17/1725 606/96 |
| 2009/0326541 A1 * | 12/2009 | Metzinger | .......... | A61B 17/1725 606/98 |
| 2010/0160913 A1 * | 6/2010 | Scaglia | ............... | A61B 17/1725 606/57 |
| 2010/0331843 A1 * | 12/2010 | Grusin | ................. | A61B 17/7225 606/64 |
| 2011/0019884 A1 * | 1/2011 | Blau | .................. | A61B 17/1703 382/128 |
| 2011/0054475 A1 * | 3/2011 | Metzinger | .......... | A61B 17/1703 606/67 |
| 2011/0054550 A1 * | 3/2011 | Metzinger | .......... | A61B 17/1703 606/86 R |
| 2011/0245885 A1 * | 10/2011 | Powell | ............... | A61B 17/1725 606/86 R |
| 2011/0270328 A1 * | 11/2011 | Overes | ............... | A61B 17/1725 606/86 R |
| 2011/0282347 A1 * | 11/2011 | Gordon | ............. | A61B 17/1725 606/64 |
| 2013/0012948 A1 * | 1/2013 | Thornes | ............. | A61B 17/1725 606/87 |
| 2013/0030444 A1 * | 1/2013 | Metzinger | .......... | A61B 17/1725 606/98 |
| 2014/0052132 A1 * | 2/2014 | Matityahu | .......... | A61B 17/1725 606/62 |
| 2014/0214045 A1 * | 7/2014 | Felder | .................... | A61B 17/72 606/104 |
| 2014/0276878 A1 * | 9/2014 | Metzinger | .......... | A61B 17/1721 606/96 |
| 2015/0038967 A1 * | 2/2015 | Khong | ................. | A61B 17/164 606/64 |
| 2017/0007303 A1 * | 1/2017 | Hansson | ............. | A61B 17/1721 |

FOREIGN PATENT DOCUMENTS

| | | |
|---|---|---|
| EP | 2606836 | 6/2013 |
| JP | 2001286481 | 10/2001 |
| WO | 03041595 | 5/2003 |
| WO | 2005096977 | 10/2005 |
| WO | 2011046784 | 4/2011 |

* cited by examiner

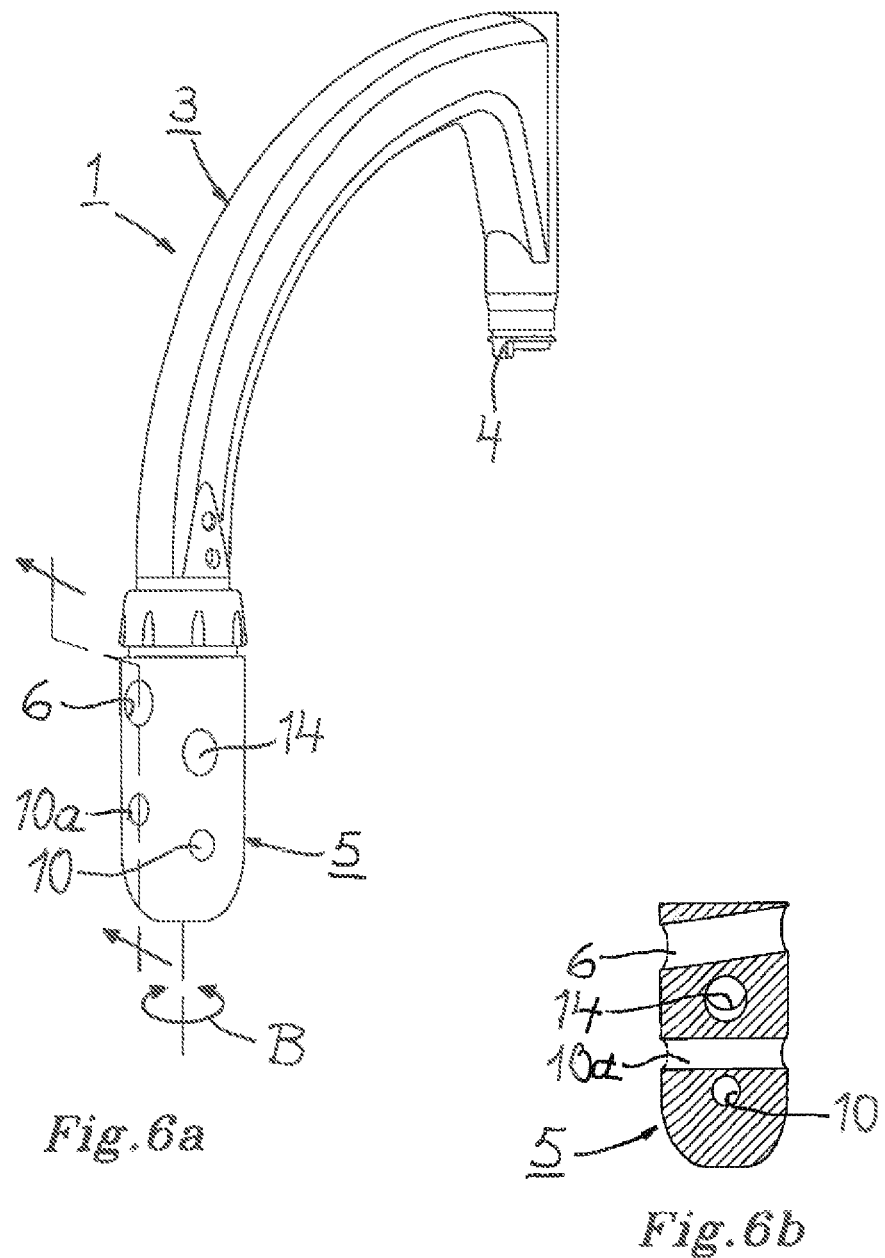

US 10,758,281 B2

TARGETING DEVICE AND METHOD

TECHNICAL FIELD

The present invention relates to a method for fixing an intramedullary cavity nail for the treatment of unstable trochanteric femur fractures. This method comprises, inter alia, the steps of inserting a cavity nail into the intramedullary canal of the femoral shaft of the fractured femur, providing a hole for a femur neck screw which extends through the femoral shaft, through an inclined proximal through-hole in the cavity nail and through the fracture into the femoral head of the fractured femur on the opposite side of the cavity nail and the fracture, providing a hole for a diaphysis screw which extends into the femoral shaft and through an oblong distal through-hole in the cavity nail into the femoral shaft on the opposite side of the cavity nail, and screwing a femur neck screw and a diaphysis screw into the respective hole therefor for fixing the cavity nail in the intramedullary canal of the femoral shaft such that withdrawal of the cavity nail therefrom is prevented.

The present invention also relates to a targeting device for use in fixing an intramedullary cavity nail for the treatment of unstable trochanteric femur fractures. The targeting device comprises a targeting arm, connection means at one free end of the targeting arm for releasably connecting a cavity nail to said connection means, and a targeting head with targeting bores at the other free end of the targeting arm. The targeting device is configured such that, when a cavity nail has been connected thereto and inserted into the intramedullary canal of the femoral shaft of the fractured femur in that order or vice versa, at least one of the targeting bores in the targeting head is alignable with an inclined proximal through-hole for a femur neck screw in the cavity nail transverse to the longitudinal axis thereof for use in providing a hole for a femur neck screw which extends through the femoral shaft, through an inclined proximal through-hole in the cavity nail and through the fracture into the femoral head of the fractured femur on the opposite side of the cavity nail and the fracture, and in screwing a femur neck screw into the hole therefor for fixing the cavity nail in the intramedullary canal of the femoral shaft such that withdrawal of the cavity nail therefrom is prevented. The targeting device is also configured such that, with a cavity nail connected thereto and inserted into the intramedullary canal of the femoral shaft as mentioned above, at least one other of the targeting bores in the targeting head is alignable with an oblong distal through-hole for a diaphysis screw in the cavity nail transverse to the longitudinal axis thereof for use in providing a hole for a diaphysis screw which extends into the femoral shaft and through the oblong distal through-hole in the cavity nail into the femoral shaft on the opposite side of the cavity nail, and in screwing a diaphysis screw into the hole therefor for fixing the cavity nail in the intramedullary canal of the femoral shaft such that withdrawal of the cavity nail therefrom is prevented.

BACKGROUND OF THE INVENTION

A targeting device for an intramedullary cavity nail substantially as defined above is already known from e.g. EP 1 455 662 B1.

The construction and function of this prior art targeting device is substantially satisfactory. However, it provides no means for assisting in eliminating the problems arising when e.g. the bone fragment or bone fragments located distally of an unstable trochanteric femur fracture, primarily the femoral shaft of the femur, and the bone fragment or bone fragments located proximally of the unstable trochanteric fracture, primarily the femoral head of the femur, during secondary compression, i.e compression after surgery, strives to be displaced, relatively seen, towards each other along the longitudinal axes of the femoral shaft and the cavity nail the-rein. During such secondary, dynamic biaxial compression of unstable trochanteric femur fractures, the compression is counteracted by the femur neck screw, because said femur neck screw, screwed into the bone fragments on both sides of the unstable trochanteric fracture, does not allow such compression.

SUMMARY OF THE INVENTION

It is therefore an object of the present invention to provide a method for fixing an intramedullary cavity nail for the treatment of unstable trochanteric femur fractures such that the at least one bone fragment located distally of the unstable trochanteric fracture, primarily the femoral shaft of the femur, and the at least one bone fragment located proximally of the unstable trochanteric fracture, primarily the femoral head of the femur, can be displaced, relatively seen, towards each other in the longitudinal direction of the femoral shaft and the cavity nail.

This is arrived at according to the invention by providing, in addition to the above-mentioned steps and in close distal proximity to the hole for the femur neck screw, a recess for the femur neck screw at least in the lateral cortex of the femoral shaft.

A further object of the present invention is to provide a targeting device for use in fixing an intramedullary cavity nail for the treatment of unstable trochanteric femur fractures, wherein said targeting device permits displacement, relatively seen, of the at least one bone fragment located distally of the unstable trochanteric fracture, primarily the femoral shaft of the femur, and the at least one bone fragment located proximally of the unstable trochanteric fracture, primarily the femoral head of the femur, towards each other in the longitudinal direction of the femoral shaft and the cavity nail.

This is arrived at according to the invention while at least one of the targeting bores in the above-mentioned targeting head is alignable with a point on the femoral shaft in close distal proximity to the hole for the femur neck screw for use in providing at said point, a recess for the femur neck screw at least in the lateral cortex of the femoral shaft.

BRIEF DESCRIPTION OF THE DRAWINGS

The invention will be further described below with reference to the accompanying drawings, in which

FIGS. 6a and 6b are a schematic perspective view of a fifth embodiment of the targeting device according to the present invention and a longitudinal section through the targeting head thereof respectively.

DETAILED DESCRIPTION OF PREFERRED EMBODIMENTS

Figure 1:
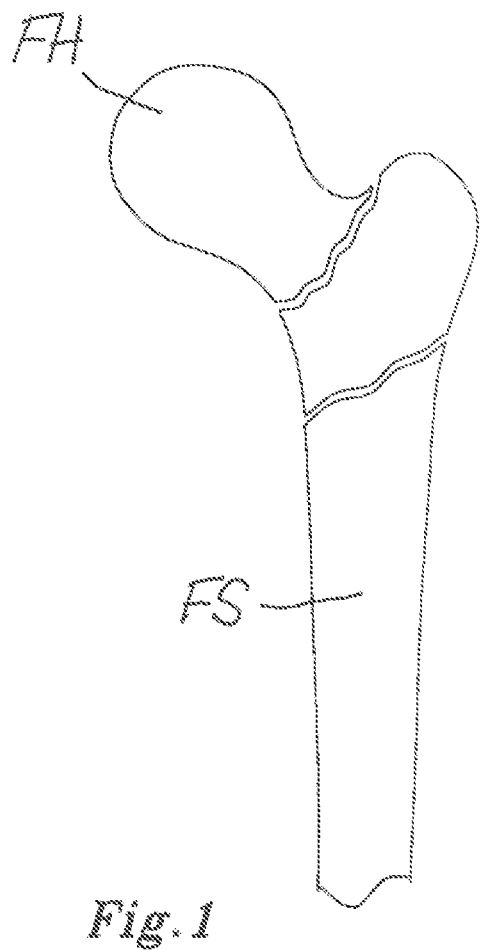
FIG. 1 is a schematic side view of an example of an unstable trochanteric fracture.

Thus, as already mentioned, the present invention relates to a method for fixing an intramedullary cavity nail for the treatment of unstable trochanteric femur fractures. The present invention also relates to a targeting device 1 for use in performing the steps of said method of fixing an intramedullary cavity nail 2 of prior art type for the treatment of unstable trochanteric femur fractures. An example of such an unstable trochanteric femur fracture is illustrated in FIG. 1. The unstable trochanteric fractures referred to in the following description are fractures located at least substantially in level with or above or proximally of the femur neck screw, with possible additional fractures involving, inter alia, the trochanter major and/or trochantor minor, e.g. unstable trochanteric fractures according to e.g. Seinsheimer 5 (combined trochantery and subtrochantery fractures).

FIG. 2-6 illustrate different embodiments of a targeting device 1, the main components of which and their function are substantially already known from e.g. EP 1 455 662 B1 and therefore not described in detail here.

The targeting device 1 comprises a targeting arm 3.

Figure 7:
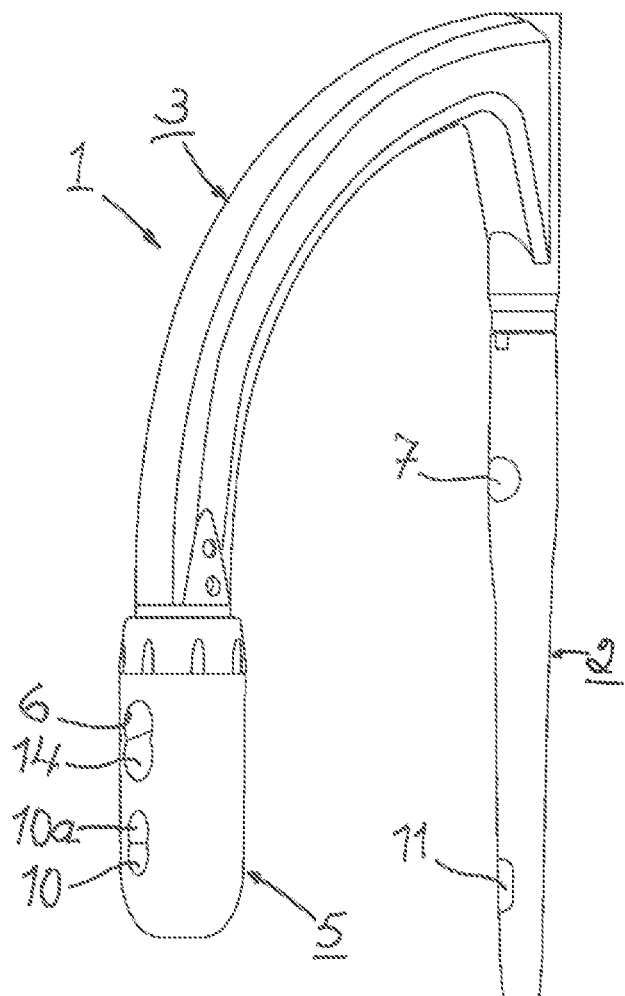
FIG. 7 is a schematic perspective view of the targeting device of FIG. 3 to which an intramedullary cavity nail is connected.

The targeting arm 3 is at one free end thereof configured with connection means 4 for releasable connection of the cavity nail 2 to said means (see FIG. 7). The connection between the cavity nail 2 and the connection means 4 can be accomplished by any suitable means, e.g. a protrusion which fits into a recess in the proximal end surface of the cavity nail, such that relative rotation of the targeting device and cavity nail is prevented. The targeting arm 3 is at the other free end thereof configured with a targeting head 5. The targeting head 5 may be releasably and/or adjustably connected to the targeting arm 3, e.g. by means of a threaded coupling or a bayonet mount or by means of e.g. screws or other means of attachment. After connection of the cavity nail 2 and the targeting head 5 to the targeting arm 3, the cavity nail and the targeting head are situated with their longitudinal axes running substantially in parallel to each other.

The targeting head 5 is in a manner known per se configured with targeting bores.

Figure 8:
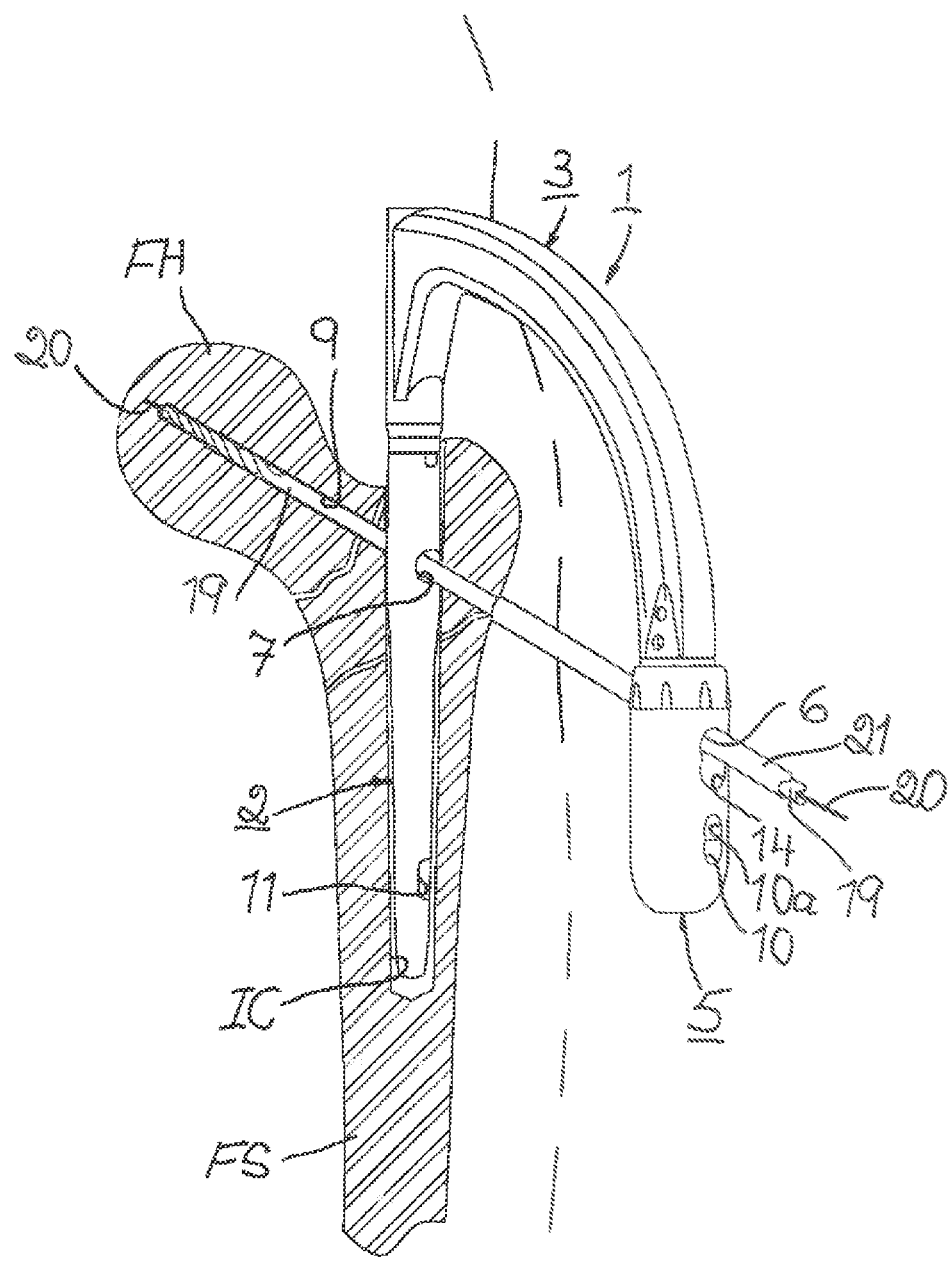
FIG. 8 is a schematic sectional view of the targeting device with the intramedullary cavity nail in position in the intramedullary canal of the femoral shaft of the fractured femur and with a drill in operation for providing the hole for the femur neck screw.

At least one of the targeting bores, in the illustrated embodiments the targeting bore 6, in the targeting head 5 is alignable with an inclined proximal through-hole 7 for a lag screw or femur neck screw 8 of prior art type in the cavity nail 2. The femur neck screw 8 may have a diameter of about 10.5 mm and a length of about 70-120 mm. The inclined proximal through-hole 7 extends transverse to the longitudinal axis of the cavity nail 2 and at an angle of e.g. about 120°, 125° or 130° relative to said longitudinal axis. Targeting bores 6 of various corresponding angles relative to the longitudinal axis of the targeting head 5 can be provided in one and the same targeting head or more than one targeting head, each having only one targeting bore 6 of a certain angle (as illustrated), may be accessible and exchangeable as desired. After insertion of the cavity nail 2 into the intramedullary canal of the femoral shaft FS of the fractured femur with the targeting device 1 already connected thereto or after insertion of said cavity nail into said intramedullary canal and then connection of the targeting device to the cavity nail, the targeting bore 6 can by means of this alignment with the inclined proximal through-hole 7 in the cavity nail be used for providing, e.g. by drilling (see FIG. 8), a hole 9 for the femur neck screw 8 which extends through the femoral shaft FS, through said inclined proximal through-hole (which thus forms part of the hole 9) in the cavity nail and through the fracture into the femoral head FH on the opposite side of the cavity nail and the fracture, and for screwing the femur neck screw into the hole therefor (see FIG. 11) for fixing the cavity nail in the intramedullary canal of the femoral shaft such that withdrawal of the cavity nail therefrom is prevented. Fixation of the cavity nail 2 as defined after insertion thereof into the intramedullary canal of the femoral shaft FS is achieved since the femur neck screw 8 is fixed at least in the femoral head FH. The femur neck screw 8 is configured such that it in position after screwing thereof into the hole 9, has a sliding engagement with the cavity nail 2 at the inclined proximal through-hole 7 therein, allowing displacement of the cavity nail relative to the femur neck screw 8 (normally a distal sliding movement of the femur neck screw 8 in the proximal through-hole 7 in the cavity nail 2) but, as indicated, preventing the cavity nail from displacement relative to the femoral shaft FS in the longitudinal direction thereof. The femur neck screw 8 may thereby also be configured in a manner known per se, e.g. configured with grooves (not illustrated) in the longitudinal direction thereof, which grooves can be engaged by a screw or pin which is inserted into the cavity nail 2 from the proximal end thereof and locked therein in a suitable manner, such that said femur neck screw is locked against rotation relative to the cavity nail and thereby prevented from unscrewing itself from its fixation in the femoral head FH.

Figure 9:
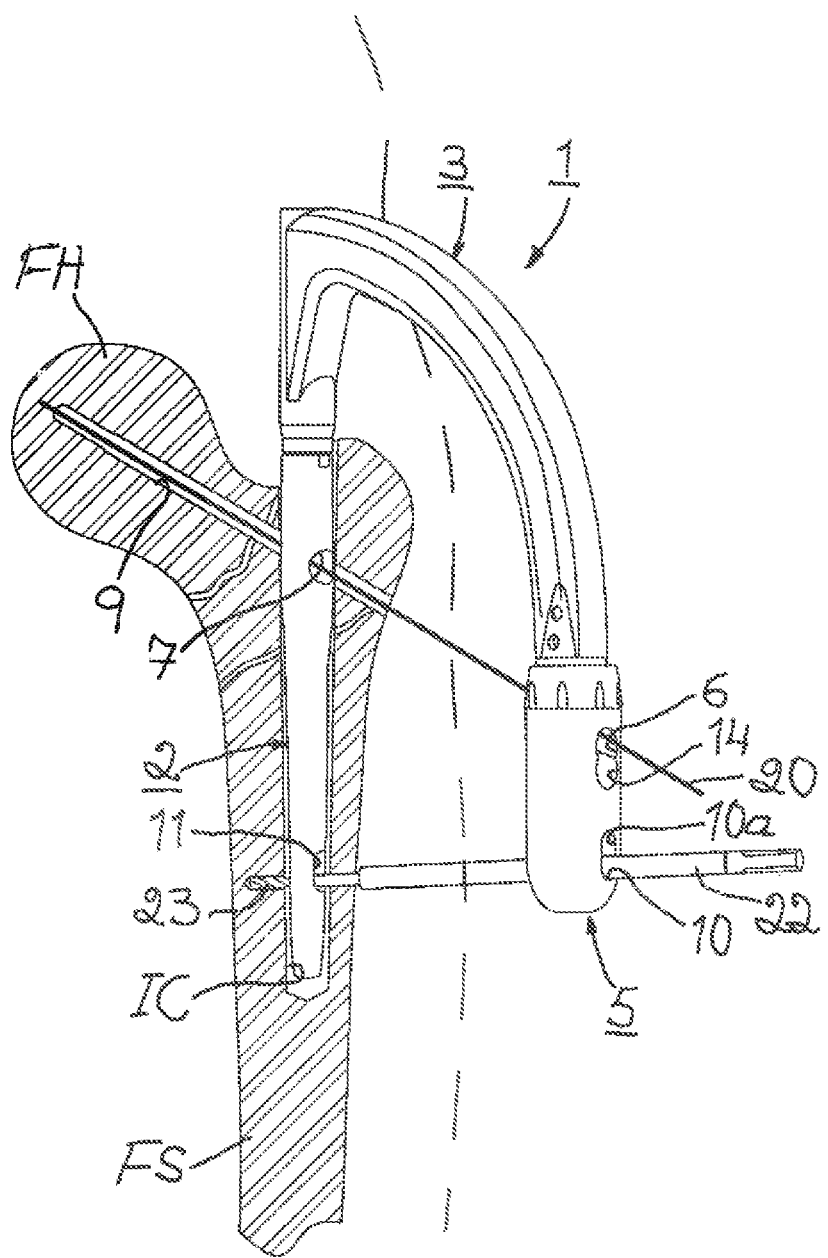
FIG. 9 is a schematic sectional view of the targeting device with the intramedullary cavity nail in position in the intramedullary canal of the femoral shaft of the fractured femur and with a drill in operation for providing the hole for the diaphysis screw.

At least one (other) of the targeting bores, in the illustrated embodiments the targeting bore 10, in the targeting head 5 is alignable with an oblong distal through-hole 11 for a distal locking screw or diaphysis screw 12 of prior art type in the cavity nail 2. The diaphysis screw 12 may have a diameter of about 5 mm and a length of about 25-50 mm. The oblong distal through-hole 11 extends also transverse to the longitudinal axis of the cavity nail 2. After insertion of the cavity nail 2 into the intramedullary canal of the femoral shaft FS of the fractured femur with the targeting device already connected thereto or after insertion of said cavity nail into said intramedullary canal and then connection of the targeting device to the cavity nail, the targeting bore 10 can by means of this alignment with the oblong distal through-hole 11 in the cavity nail be used for providing, e.g. by drilling (see FIG. 9), a hole 13 for the diaphysis screw 12 which extends into the femoral shaft FS and through the oblong distal through-hole (which thus forms part of the hole 13) in the cavity nail into the femoral shaft on the opposite side of the cavity nail, and for screwing the diaphysis screw into the hole therefor (see FIG. 12) for fixing the cavity nail in the intramedullary canal of the femoral shaft such that withdrawal of the cavity nail therefrom is prevented. The targeting bore 10 may extend through the targeting head 5 at any suitable angle relative to the longitudinal axis of the targeting head, also substantially perpendicular thereto. Fixation of the cavity nail 2 as defined after insertion thereof into the intramedullary canal of the femoral shaft FS is achieved since the diaphysis screw 12 is fixed in the femoral shaft. However, the oblong through-hole 11, permits during secondary compression minor displacements (dynamic locking) of the cavity nail 2 relative to the femoral shaft FS in the longitudinal direction thereof if the diaphysis screw is locked in the distal part of the oblong through-hole. Static locking of the cavity nail 2 is allowed if the diaphysis screw 12 is inserted and locked in the proximal part of the oblong through-hole 11.

According to the present invention, the targeting head 5 is further configured with at least one targeting bore 14 which is alignable with a point in close distal proximity to the hole 9 for the femur neck screw 8 (see FIG. 3). This targeting bore 14 is in all the illustrated embodiments configured for receiving a working tool 15 therein, either directly or indirectly via a guide for the working tool.

Figure 10:
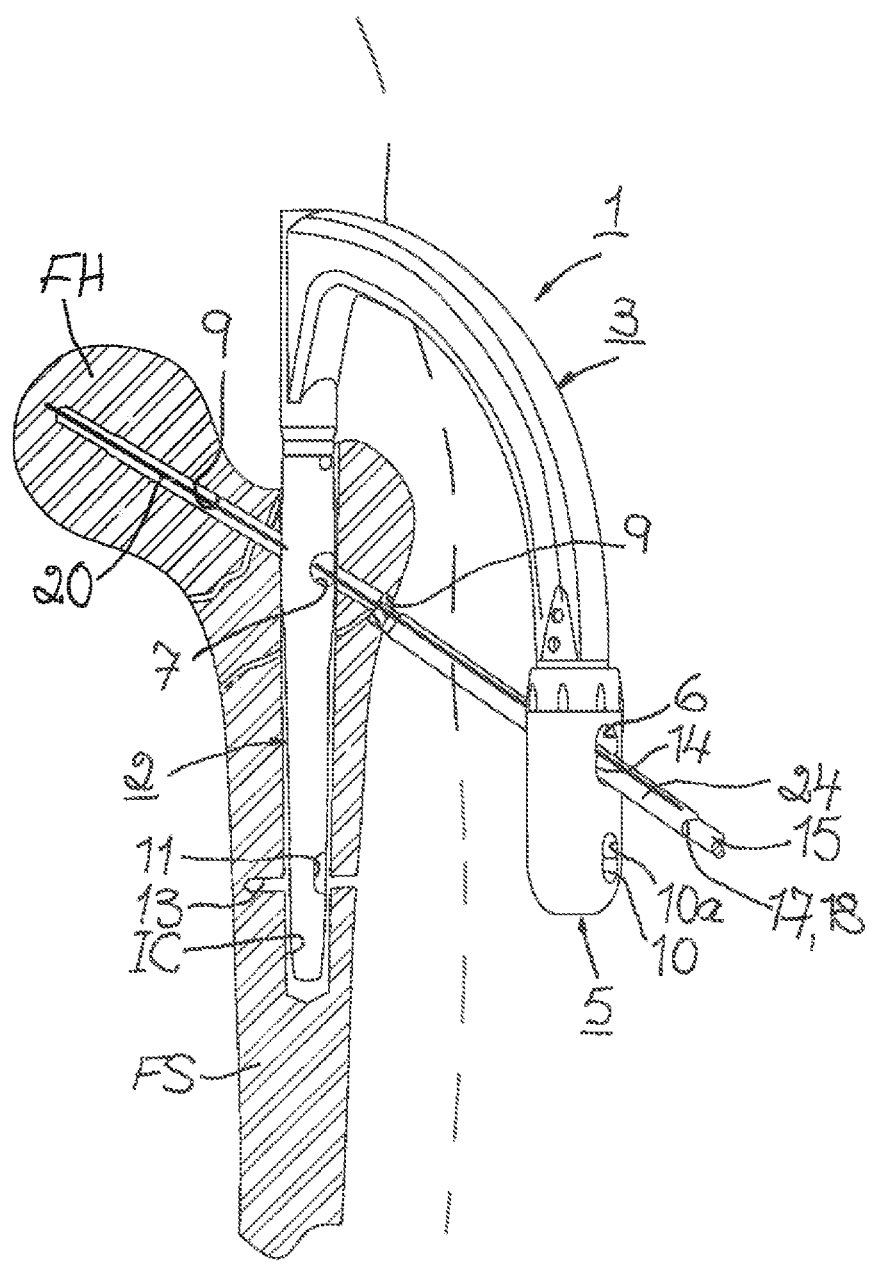
FIG. 10 is a schematic sectional view of the targeting device with the intramedullary cavity nail in position in the intramedullary canal of the femoral shaft of the fractured femur and with a working tool in operation for providing the recess.
Figure 14:
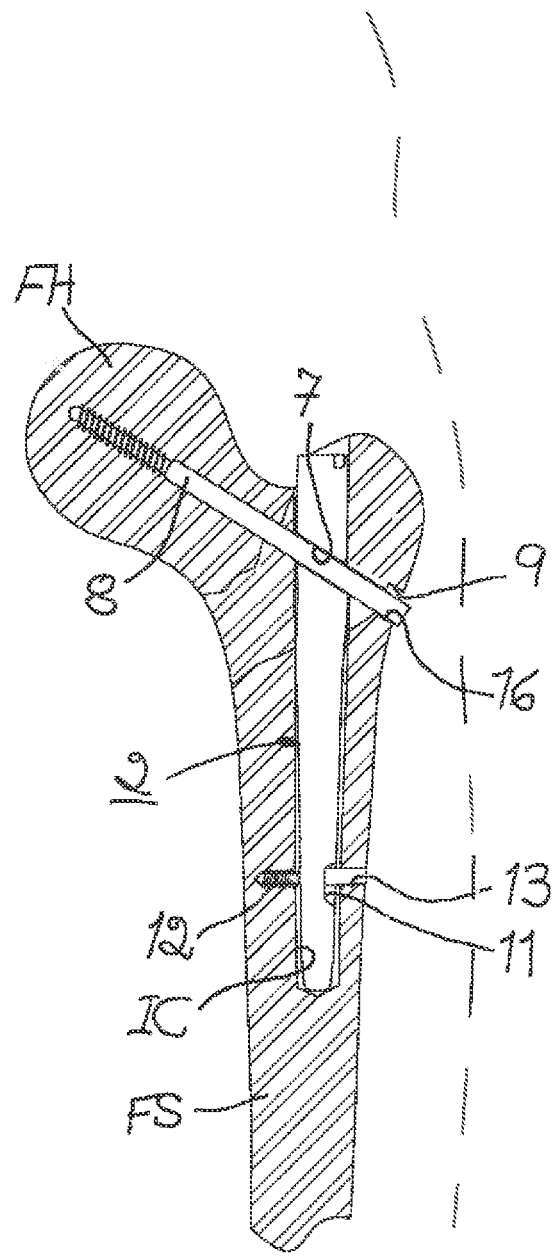
FIG. 14 is a schematic sectional view of the intramedullary cavity nail in position in the intramedullary canal of the femoral shaft of the fractured femur after secondary compression of the bone fragments.

Thus, the working tool 15, e.g. a manually operated or power-operated cutter, is configured for providing in close distal proximity to the hole 9 for the femur neck screw 8, i.e. when the cavity nail 2 already has been inserted into the intramedullary canal of the femoral shaft FS and said hole for the femur neck screw already has been provided (FIG. 8), a recess 16 for the femur neck screw in at least the lateral cortex of the fractured femur in close distal proximity to the entry portion of said hole in the femoral shaft of the fractured femur (FIG. 10). The recess 16 for the femur neck screw 8 will thereby provide space for at least the portion of said femur neck screw located in the lateral cortex of the fractured femur, i.e. the lateral cortex of the part of the femoral shaft FS distally adjacent the hole 9 for the femur neck screw, such that, during secondary compression as illustrated in FIG. 14, the at least one bone fragment located distally of the unstable trochanteric fracture, primarily the femoral shaft, and the at least one bone fragment located proximally of the unstable trochanteric fracture, primarily the femoral head FH, relatively seen can be displaced towards each other in the longitudinal direction of the femoral shaft and the cavity nail (normally accomplished by displacement of the cavity nail distally in the intramedullary canal in the femoral shaft). Thus, since the lateral cortex consists of compact bone tissue which can counteract or even prevent desired secondary compression of the bone fragments, the recess 16 is critical for allowing secondary compression without problems and thereby achieve optimum healing of the fracture. If desired, the recess 16 can be made to run deeper into the bone tissue, past the compact bone tissue in the lateral cortex of the femoral shaft FS and into the spongy bone tissue thereof. In fact, the recess 16 may run all the way into the cavity nail 2 in the intramedullary canal of the femoral shaft FS. Secondary compression is possible also thanks to the oblong distal through-hole 11 for the diaphysis screw 12 in the cavity nail 2, allowing displacement of said diaphysis screw with the bone fragment distally of the unstable trochanteric fracture, particularly the femoral shaft FS, relative to the cavity nail or normally, as indicated above, distal displacement of the cavity nail 2 relative to the diaphysis screw. Preferably, the targeting bore 14 or the guide (guide sleeve 24; see FIG. 10) for a working tool 15 received in said targeting bore is configured with a stop means 17 for engagement by a mating stop means 18 on the working tool for limiting the depth of the recess 16 provided in at least the lateral cortex of the femoral shaft FS. These stop means 17, 18 can be configured in many ways, e.g. as collars or protrusions on the respective instrument as illustrated in FIG. 10. It should also be noted that the recess 16 for the femur neck screw 8 is provided preferably after provision of the hole 9 for said femur neck screw, but before screwing the femur neck screw into said hole. However, it is in some embodiments possible to provide the recess 16 for the femur neck screw 8 also after screwing the femur neck screw into the hole 9 therefor.

Figure 13:
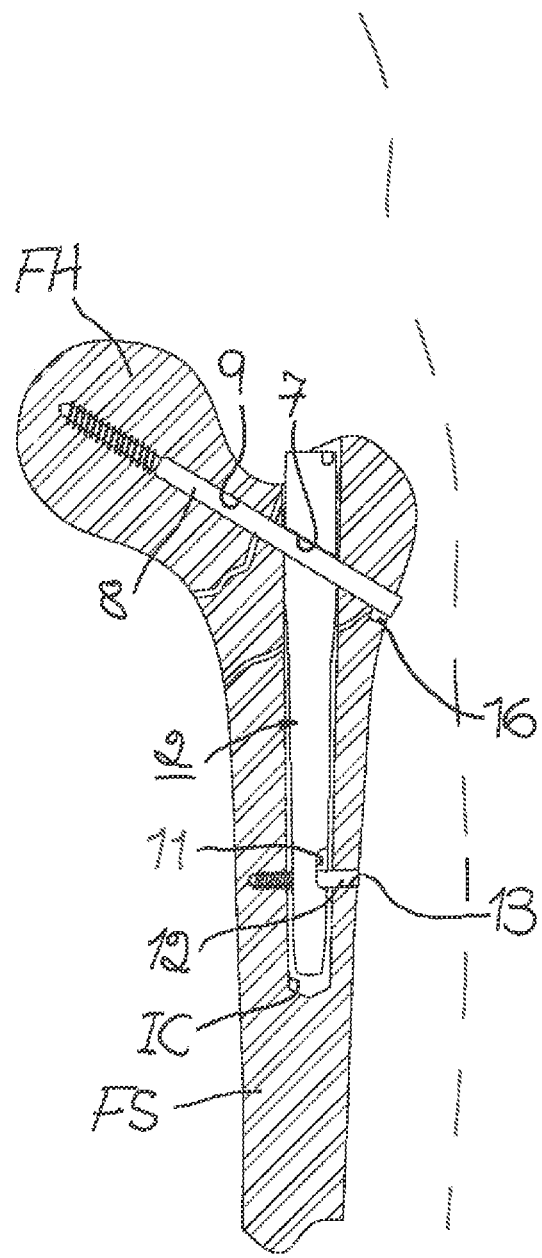
FIG. 13 is a schematic sectional view of the intramedullary cavity nail in position in the intramedullary canal of the femoral shaft of the fractured femur after removal of the targeting device.

With the provision of the recess 16, secondary compression may as indicated above be biaxial, i.e. compression along the femur neck screw 8 as well as in the longitudinal direction of the femoral shaft FS/cavity nail 2 is permitted. The at least one bone fragment located proximally of the unstable trochanteric fracture, in FIG. 13 primarily the femoral head FH, and the at least one bone fragment located distally of the unstable trochanteric fracture, in FIG. 13 primarily the femoral shaft FS, will then be displaceable relative to each other by permitting sliding of the former, with femur neck screw 8, in the cavity nail 2, and said at least one bone fragment located proximally of the unstable trochanteric fracture (the femoral head FH) will with the cavity nail 2 and the femur neck screw 8 be displaceable in the longitudinal direction of the bone fragment distally of the unstable trochanteric femur fracture (the femoral shaft FS), as illustrated in FIG. 14. The displacement of the portion of the femur neck screw 8 located primarily in the lateral cortex of the femoral shaft FS is not, thanks to the recess 16, counteracted during the displacement of the cavity nail 2 relative to primarily the femoral shaft. Without the recess 16, secondary compression is primarily uniaxial, i.e. substantially problem-free compression is possible only in the longitudinal direction of the femur neck screw 8, unless said femur neck screw and the cavity nail 2 are configured to engage each other for preventing such relative displacement thereof.

It is important to note that the relative compressions/displacements referred to above of the bone fragments and/or of the cavity nail and the screws used therewith towards and/or relative to each other, can be achieved by compression forces from various possible directions. Based on from which direction a compression force is applied, different bone fragments and/or the cavity nail and/or the screws used therewith are compressed/displaced, but the compressions/displacements of the bone fragments and/or the cavity nail and/or the screws for the cavity nail relative to each other remain the same. However, it is most probable that secondary compression occurs when a patient after surgery has begun to stand up and walk around, thereby generating compression forces from above, pressing the femoral head FH towards the femoral shaft FS such that the femur neck screw 8 thereby performs a sliding movement relative to the cavity nail 2 and the cavity nail along with the femur neck screw are displaced downwards/distally relative to the femoral shaft. The femur neck screw 8 is then also displaced from the upper/proximal end towards the lower/distal end of the recess 16 and the cavity nail 2 is displaced such that the diaphysis screw 12 in the oblong through-hole 11 in the cavity nail seems to move from the distal end of said oblong through-hole towards the proximal end thereof.

The at least one targeting bore 14 for the working tool 15 for providing the recess 16 for the femur neck screw 8 can be configured in different ways in the targeting head in order to see to that the recess is provided in close distal proximity to the hole 9 provided in the femoral shaft FS for the femur neck screw 8, forming an oblong recess therewith.

Figure 2A:
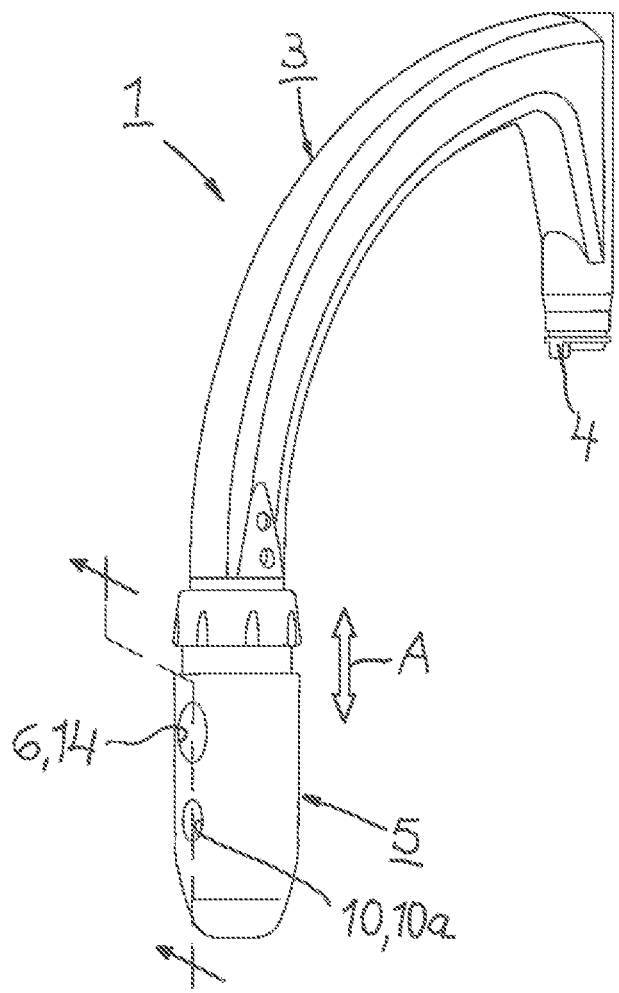
FIGS. 2a and 2b are a schematic perspective view of a first embodiment of the targeting device according to the present invention and a longitudinal section through the targeting head thereof respectively.
Figure 2B:
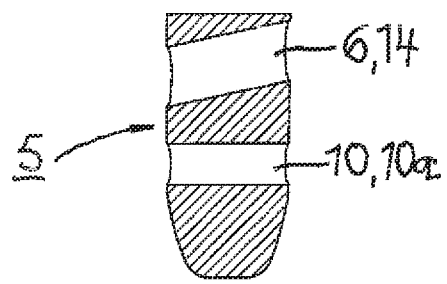

Thus, in one possible embodiment according to FIGS. 2a and 2b, wherein the targeting arm 3 and the targeting head 5 are configured with mating connection means which are configured to permit adjustment of the targeting head in its longitudinal direction (indicated by the double arrow A), the at least one targeting bore 6 for use in providing the hole 9 for the femur neck screw 8 and the at least one targeting bore 14 for use in providing the recess 16 for the femur neck screw are made up of one and the same targeting bore. Before adjustment of the targeting head 5, the targeting bore 6 may be used for providing the hole 9 for the femur neck screw 8. After adjustment in the longitudinal direction of the targeting head 5, distally along the femur/cavity nail 2, the recess 16 may be provided by means of the targeting bore 6. Adjustment may of course also be performed in the opposite direction, proximally along the femur/cavity nail 2, but the hole 9 for the femur neck screw 8 is preferably provided before provision of the recess 16. Accordingly, in such an embodiment, the targeting head 5 may be configured with only two targeting bores, namely targeting bores 6 and 10.

The at least one targeting bore 14 for the working tool 15 for providing the recess 16 for the femur neck screw 8 can alternatively be configured as a bore which is totally or partly separated from the at least one targeting bore 6 for use in providing the hole 9 for the femur neck screw 8. The targeting bore 14 is also totally separated from the at least one bore 10 for use in providing the hole 13 for the diaphysis screw 12.

Figure 3A:
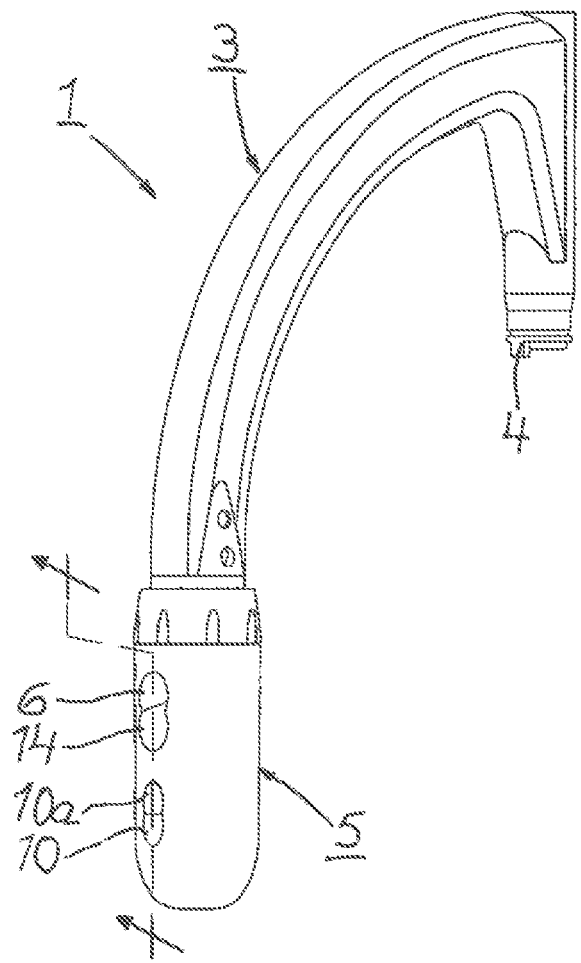
FIGS. 3a and 3b are a schematic perspective view of a second embodiment of the targeting device according to the present invention and a longitudinal section through the targeting head thereof respectively.
Figure 3B:
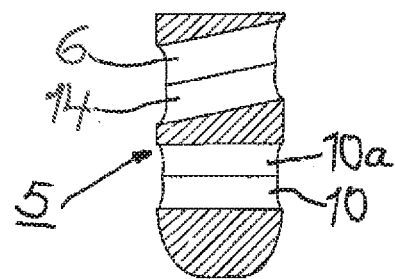

As illustrated in FIGS. 3a and 3b, the at least one targeting bore 14 for use in providing the recess 16 for the femur neck screw may thereby be provided in the targeting head 5 in the same longitudinal plane through the targeting head as the at least one targeting bore 6 for use in providing the hole 9 for the femur neck screw 8 and such that it intersects, with the upper peripheral part thereof, the lower peripheral part of said latter targeting bore. In such an embodiment, the targeting head 5 may be configured with only three targeting bores, namely targeting bores 6, 10 and 14, of which targeting bores 6 and 14 coincide partly with each other, thereby providing an oblong combined bore/recess.

Figure 4A:
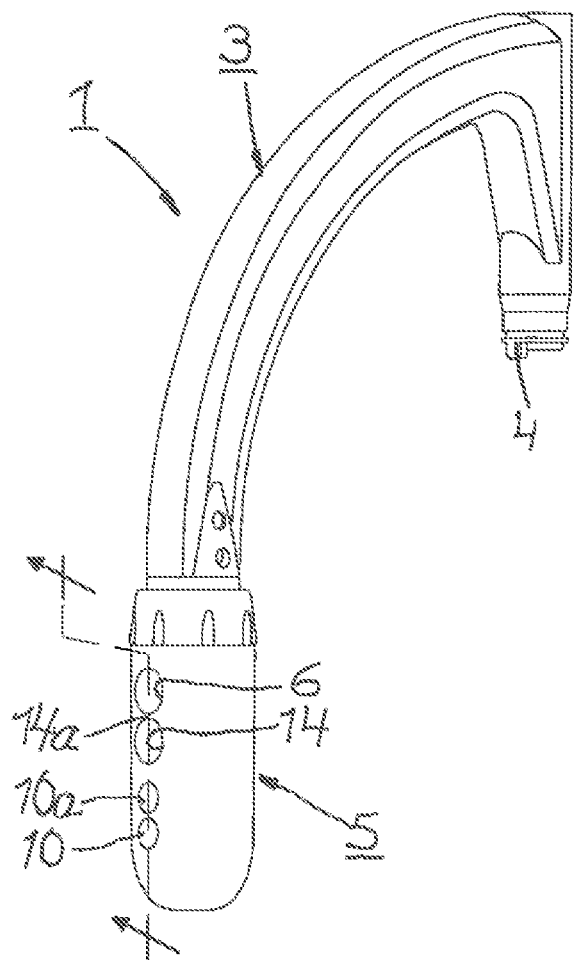
FIGS. 4a and 4b are a schematic perspective view of a third embodiment of the targeting device according to the present invention and a longitudinal section through the targeting head thereof respectively.
Figure 4B:
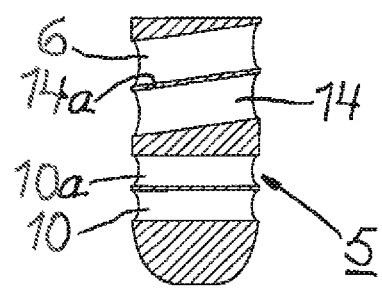

The at least one targeting bore 14 for the working tool 15 for providing the recess 16 for the femur neck screw 8 can according to another alternative be provided in the targeting head 5 in the same longitudinal plane through the targeting head as the at least one targeting bore 6 which is alignable with the inclined proximal through-hole 7 for the femur neck screw 8 in the cavity nail 2 for use in providing the hole 9 for said femur neck screw, at a distance therefrom and in parallel therewith (see FIGS. 4a and 4b). As in FIGS. 3a and 3b, with the targeting device 1 in position for use, the targeting bore 14 is situated distally of the targeting bore 6, but is not intersecting any part thereof. Instead, the targeting bore 14 is situated very close to and yet separated from the targeting bore 6 by a very thin, breakable partition 14a. In this embodiment, the targeting head 5 may also be configured with only three targeting bores, namely targeting bores 6, 10 and 14, which are all separated from each other.

Figure 5A:
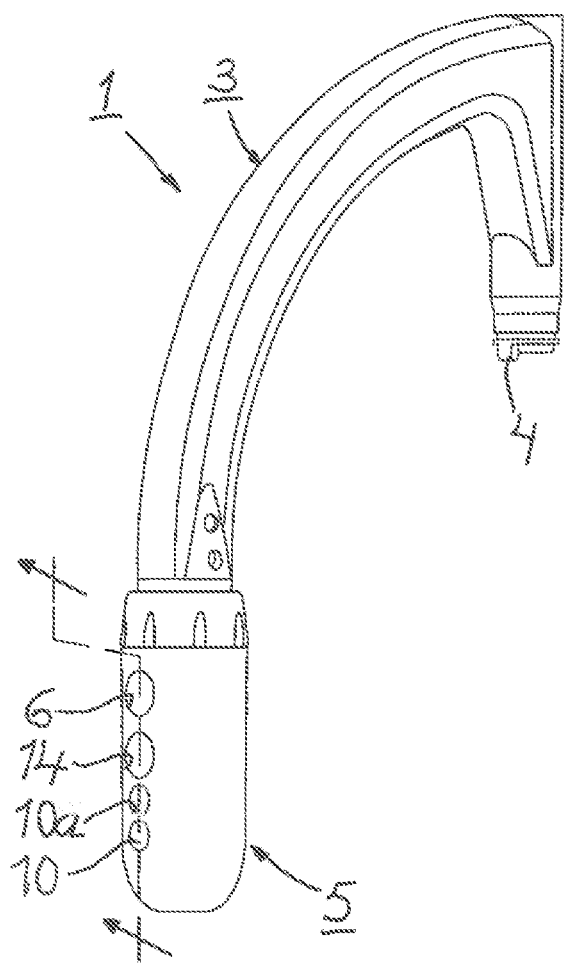
FIGS. 5a and 5b are a schematic perspective view of a fourth embodiment of the targeting device according to the present invention and a longitudinal section through the targeting head thereof respectively.
Figure 5B:
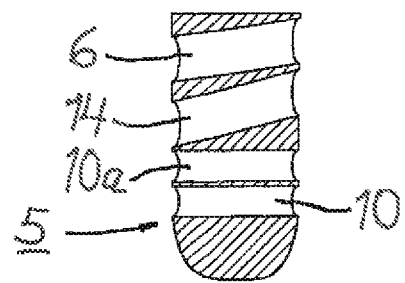

Alternatively thereto, as illustrated in FIGS. 5a and 5b, the targeting bore 14 for the working tool 15 for providing the recess 16 for the femur neck screw 8 is again provided in the targeting head 5 in the same longitudinal plane through the targeting head as the at least one targeting bore 6 which is alignable with the inclined proximal through-hole 7 for the femur neck screw 8 in the cavity nail 2 for use in providing the hole 9 for said femur neck screw, but now also at an angle relative to said at least one targeting bore instead of in parallel therewith, as in FIGS. 4a and 4b. If e.g. the targeting bore 6 of the targeting head 5, aligned with the inclined through-hole 7, has an angle of about 125° relative to the longitudinal axis of the targeting head, then the targeting bore 14 for use in providing the recess 16 in the targeting head may have an angle of e.g. about 130° relative to said longitudinal axis of the targeting head. The distance between the targeting holes 6, 14 may then be somewhat larger than in the above-mentioned embodiments, i.e. larger than the combined length of the hole 9 and the recess 16.

With this latter embodiment, it is also possible to alternatively configure the targeting bore 14 for use in providing the recess 16 for the femur neck screw 8 such that it e.g. crosses the at least one targeting bore 6 for use in providing the hole 9 for the femur neck screw such that said former targeting bore at its inlet opening, on the side of the targeting head 5 facing away from the cavity nail 2, is located above/proximally of the inlet opening of said latter targeting bore and at its outlet opening, on the side of the targeting head facing the cavity nail, is located beneath/distally of the outlet opening of said at least one targeting bore. This alternative embodiment however, requires that there is no guide or drill or screw occupying the targeting bore 6 when the recess 16 is provided.

Another alternative (similar to that of FIGS. 4a and 4b), wherein the targeting arm 3 and the targeting head 5 are configured with mating connection means which in turn are configured to permit rotation of the targeting head about its longitudinal axis (indicated by the double arrow B), is to provide the at least one targeting bore 14 for the working tool 15 for providing the recess 16 for the femur neck screw 8 in the targeting head in another longitudinal plane through the targeting head as the at least one targeting bore 6 which is alignable with the inclined proximal through-hole 7 for the femur neck screw 8, at a distance therefrom and in parallel therewith (see FIGS. 6a and 6b). As in FIGS. 4a and 4b, with the targeting device 1 in position for use, the targeting bore 14 is situated distally of the targeting bore 6, in vertical direction very close to the targeting bore 6. Thus, in one rotary position of the targeting head 5, the targeting bore 6 is aligned with the inclined proximal through-hole 7 in the cavity nail 2 and, after rotation to another rotary position of the targeting head, the targeting bore 14 is aligned with the point on the femoral shaft FS in close distal proximity to the hole 9 for the femur neck screw 8. The rotary movement for performing the above-mentioned function may vary as desired, e.g. be about 90° as in FIGS. 6a and 6b.

According to a still other alternative, wherein the targeting arm 3 and the targeting head 5 are configured with mating connection means which in turn are configured to permit rotation of the targeting head about its longitudinal axis, as in the embodiment of FIGS. 6a and 6b, the at least one targeting bore 14 for the working tool 15 is provided in the targeting head in another longitudinal plane through the targeting head as and at an angle relative to the at least one targeting bore 6 which is alignable with the inclined proximal through-hole 7 for the femur neck screw 8. This is an alternative to the embodiment of FIGS. 5a and 5b with non-parallel targeting bores. Here again, the targeting bore 6 is in one rotary position of the targeting head 5 aligned with the inclined proximal through-hole 7 in the cavity nail 2 and, after rotation to another rotary position of the targeting head, the targeting bore 14 is aligned with the point on the femoral shaft FS in close distal proximity to the hole 9 for the femur neck screw 8. It is here also possible to configure the targeting bore 14 such that it e.g. crosses the at least one targeting bore 6 such that said former targeting bore at its inlet opening, on the side of the targeting head 5 facing away from the cavity nail 2, is located above/proximally of the inlet opening of said latter targeting bore and at its outlet opening, on the side of the targeting head facing the cavity nail, is located beneath/distally of the outlet opening of said latter targeting bore. On the other hand, it is also possible to let the vertical distance between the targeting holes 6, 14 be somewhat larger than the combined length of the hole 9 and the recess 16.

Combinations of the above-mentioned embodiments are possible, with e.g. targeting heads 5 which are rotatable as well as adjustable in the longitudinal direction thereof.

The targeting bore 14 for use in providing the recess 16 for the femur neck screw 8 is configured to provide, by means of the working tool received therein, a recess 16 with a length of 5-10 mm, preferably about 7 mm. This is considered to be sufficient for permitting most cases of secondary compression and fits the size of most femur neck screws 8. The length of the recess 16 should also preferably correspond to the length of the oblong distal through-hole 11 in the cavity nail 2. The easiest way to provide a recess of such length is to configure the targeting bore 14 for receiving therein a working tool 15 with a diameter of 5-10 mm, preferably about 7 mm and thereby directly provide a recess with the same diameter. Together with the hole 9, the recess 16 thereby defines an oblong combined hole/recess in at least the lateral cortex of the femoral shaft FS, as already stated above.

As already indicated above, the at least one targeting bore 10 for use in providing the hole 13 for the diaphysis screw 12 is alignable with the oblong distal through-hole 11 for said diaphysis screw in the cavity nail 2 such that relative displacement of the at least one bone fragment located distally of the unstable trochanteric fracture, primarily the femoral shaft FS, and the at least one bone fragment located proximally of the unstable trochanteric fracture, primarily the femoral head FH, towards each other in the longitudinal direction of the femoral shaft and the cavity nail 2 is permitted (dynamic locking of the cavity nail).

However, it may under certain circumstances be advantageous to provide for static locking of the cavity nail 2 and thus, only uniaxial compression along the femur neck screw 8 or no compression at all if the femur neck screw is prevented from displacement relative to the cavity nail. It is therefore an advantage if the targeting head 5 defined above can be configured such that it is possible to choose between dynamic and static locking of the cavity nail 2. To accomplish this, the targeting head 5 can be configured in various ways.

Accordingly, in one embodiment where, as mentioned above, the targeting arm 3 and the targeting head 5 are configured with mating connection means which are configured to permit adjustment of the targeting head in its longitudinal direction (see FIGS. 2a and 2b; double arrow A), the at least one targeting bore 10 for use in providing the hole 13 for the diaphysis screw 12 is alignable with the oblong distal through-hole 11 for said diaphysis screw in the cavity nail such that relative displacement of the at least one bone fragment located distally of the unstable trochanteric fracture, primarily the femoral shaft FS, and the at least one bone fragment located proximally of the unstable trochanteric fracture, primarily the femoral head FH, towards each other in the longitudinal direction of the femoral shaft and the cavity nail 2 is not permitted. This means that the targeting bore 10, with the targeting device 1 connected to the cavity nail 2, can be adjusted from a position where it is alignable with the distal part of the oblong through-hole 11 in the cavity nail 2 (dynamic locking of the cavity nail) to a position where said targeting bore is alignable with the proximal part of said oblong through-hole (static locking of the cavity nail). Adjustment may also be performed in the opposite direction, from said latter position to said former position. As already mentioned, adjustment is performed in the longitudinal direction of the targeting head 5, along the femur/cavity nail 2. In this embodiment, the targeting head 5 may still be configured with only two targeting bores, namely targeting bores 6 and 10.

Alternatively, the targeting head 5 may be configured with two targeting bores 10 and 10a for use in providing the hole 13 for the diaphysis screw 12. One of said targeting bores, targeting bore 10, is alignable with the oblong distal through-hole 11 for said diaphysis screw 12 in the cavity nail 2 such that relative displacement of the at least one bone fragment located distally of the unstable trochanteric fracture, primarily the femoral shaft FS, and the at least one bone fragment located proximally of the unstable trochanteric fracture, primarily the femoral head FH, towards each other is permitted (dynamic locking of the cavity nail). The other of said targeting bores, targeting bore 10a, is then alignable with the oblong distal through-hole 11 for said diaphysis screw 12 in the cavity nail 2 such that relative displacement of the at least one bone fragment located distally of the unstable trochanteric fracture, primarily the femoral shaft FS, and the at least one bone fragment located proximally of the unstable trochanteric fracture, primarily the femoral head FH, towards each other in the longitudinal direction of the femoral shaft and the cavity nail is not permitted (static locking of the cavity nail). This means that the targeting bore 10 is alignable with the distal part of the oblong through-hole 11 in the cavity nail 2 and the targeting bore 10a is alignable with the proximal part of said oblong through-hole.

The two targeting bores 10, 10a for use in providing the hole 13 for the diaphysis screw 12 can be provided in the targeting head 5 such that they are totally or partly separated from each other. The two targeting bores 10, 10a are also totally separated from the at least one targeting bore 6 for use in providing the hole 9 for the femur neck screw 8 and, if a separate targeting bore 14 for use in providing the recess 16 for the femur neck screw is present, totally separated also from this latter targeting bore. Thus, the targeting head 5 may be configured with only three targeting bores, namely targeting bores 6, 10 and 10a, or with four targeting bores, namely targeting bores 6, 10, 10a and 14, of which targeting bores 6 and 14 coincide partly with each other or are totally separated from each other. As with said targeting bores 6, 14, the two targeting bores 10, 10a for use in providing the hole 13 for the diaphysis screw 12 can be provided in the targeting head 5 such that the upper peripheral part of one of said targeting bores, i.e. targeting bore 10, intersects with the lower peripheral part of the other of said targeting bores, targeting bore 10a (see FIGS. 3a and 3b). If separate, the two targeting bores 10, 10a are preferably provided in the targeting head 5 at a distance from each other in the same longitudinal plane through the targeting head and in parallel with each other. This distance corresponds preferably to the length of the oblong through-hole 11 in the cavity nail 2 and may accordingly vary depending on said length of the oblong through-hole (see FIGS. 4 and 4b and 5a and 5b respectively). Alternatively, if the targeting arm 3 and the targeting head 5 as in FIGS. 6a and 6b are configured with mating connection means which are configured to permit rotation of the targeting head about its longitudinal axis (double arrow B), then the two targeting bores 10, 10a for use in providing the hole 11 for the diaphysis screw 12 may be provided in the targeting head 5 at a distance from each other, in two different longitudinal planes through the targeting head and in parallel with each other. As above, the vertical distance between the two targeting bores 10, 10a corresponds preferably to the length of the oblong through-hole 11 in the cavity nail 2 and may accordingly vary depending on said length of the oblong through-hole. Thus, with a rotatable targeting head 5 and with the targeting device 1 in position for use, the targeting bore 10 may in one rotary position of the targeting head 5 be aligned with the distal part of the oblong through-hole 11 in the cavity nail 2 (dynamic locking of the cavity nail) and, after rotation of the targeting head to another rotary position, the targeting bore 10a may be aligned with the proximal part of said oblong through-hole (static locking of the cavity nail).

Combinations of the above-mentioned embodiments are possible, with targeting heads 5 which are rotatable as well as adjustable in the longitudinal direction thereof.

In short, fixing of the intramedullary cavity nail 2 can be carried through by, initially, after proper positioning of the patient and reduction of the fracture and after having performed necessary incision and other preparations for exposing the femur, opening the intramedullary canal IC of the femur (femoral shaft FS) and inserting the cavity nail 2 into said intramedullary canal. It may thereby be necessary to first widen (e.g. by reaming, cutting or drilling) the intramedullary canal or parts thereof. There must be sufficient place in the intramedullary canal IC for relative displacement of the cavity nail 2 and the femoral shaft FS, i.e. the cavity nail must be allowed to be displaced about 5-10 mm, preferably about 7 mm, relative to the femoral shaft. The targeting device 1 may then be connected to the cavity nail 2 or it may preferably already be connected (see FIG. 7) when the cavity nail is inserted into the intramedullary canal IC of the femoral shaft FS of the fractured femur, because it is then possible to control that all targeting bores 6, 10, 10a, 14 provided in the targeting head 5 are aligned with the holes 7, 11 in the cavity nail and with a point or portion of the femoral shaft FS in close distal proximity to the hole 9 for the femur neck screw 8. After insertion of the cavity nail 2 into the intramedullary canal IC of the femur, the alignment of the targeting bore 6 in the targeting head 5 with the proximal through-hole 7 in the cavity nail 2 should be maintained by the relative locking of the cavity nail and the targeting device 1 to each other. The position of the cavity nail 2 in the intramedullary canal IC and possibly, the position of a femur neck screw to be inserted, is controlled. A lateral skin incision down to the bone is made and a drill guide sleeve is inserted into the targeting bore 6 and brought in contact with the lateral cortex of the femur (femoral shaft FS) for an accurate measurement of the femur neck screw length. A drill is inserted into the drill guide sleeve and the lateral cortex is opened. The drill guide sleeve is removed and replaced by a wire guide sleeve. A K-wire is inserted into the wire guide sleeve and advanced up to the subchondral bone in the femoral head FH manually or by means of a power tool. The required femur neck screw length is measured. The wire guide sleeve is removed and a drill 19 is threaded onto the K-wire 20 through the drill guide sleeve 21. The measured length of the femur neck screw is set on the drill 19 and the hole 9 for the femur neck screw 8 is now provided until the stop means on the drill comes in contact with the rear end of the drill guide sleeve 21. This is the situation illustrated in FIG. 8. The procedure should be controlled under an image intensifier to avoid hip joint penetration. The tip of the K-wire 20 should be set to protrude about 6-10 mm out of the drill 19, because the threaded portion of the K-wire was not included in the drill (femur neck screw) length measurement. The drill 19 is removed, but in the embodiments of FIG. 3-5, the K-wire 20 may remain seated in the hole 9.

The procedure for providing the hole 13 for the diaphysis screw 12 is partly the same as for providing the hole 9 for the femur neck screw 8 described above. Thus, after insertion of the cavity nail 2 into the intramedullary canal IC of the femoral shaft FS of the fractured femur, the alignment of the targeting bore 10 (10a) in the targeting head 5 with the oblong through-hole 11 in the cavity nail 2 should still be maintained by the relative locking of the cavity nail and the targeting device 1 to each other. The position of the cavity nail 2 in the intramedullary canal IC and possibly, the position of a diaphysis screw to be inserted, is controlled. A lateral skin incision down to the bone is made and a drill guide sleeve 22 with a trocar is inserted into the targeting bore 10 (10a) and brought in contact with the lateral cortex of the femoral shaft and locked. The trocar is removed and the drill 23 is inserted into the drill guide sleeve 22 and operated. The first lateral cortex is opened and drilling proceeds until the second lateral cortex is reached or drilled through. This is the situation illustrated in FIG. 9. A measurement of the required screw length is made. The procedure may be controlled under an image intensifier. The drill 23 is removed, but may in the embodiments of FIG. 3-5 remain seated in the hole 13. Alternatively, if desired, the diaphysis screw 12 may already now be attached by screwing said screw into the hole 13.

The procedure for providing the recess 16 for the femur neck screw 8 is partly the same as for providing the hole 9 for the femur neck screw 8 described above. Again, after insertion of the cavity nail 2 into the intramedullary canal IC of the femoral shaft FS of the fractured femur, the alignment of the targeting bore 14 in the targeting head 5 with the portion of the femoral shaft FS in close distal proximity to the hole 9 for the femur neck screw 8 should be maintained by the relative locking of the cavity nail and the targeting device 1 to each other. The position of the cavity nail 2 in the intramedullary canal IC and the position of the working tool for providing the recess 16 is controlled. A lateral skin incision down to the bone is made and a working tool guide sleeve 24 is inserted into the targeting bore 14 and brought in contact with the lateral cortex of the femoral shaft FS. A measurement of the working tool length is performed. A working tool 15, e.g. a cutter, a drill or a chisel is inserted into the working tool guide sleeve 24 and the recess 16 in at least the lateral cortex is provided. This is the situation illustrated in FIG. 10. The depth of the recess 16 is controlled by the length set on the working tool 15 and provision of the recess is continued until the stop means 18 on the working tool comes in contact with the stop means 17 at the rear end of the working tool guide sleeve 24. The working tool 15 is removed.

Figure 11:
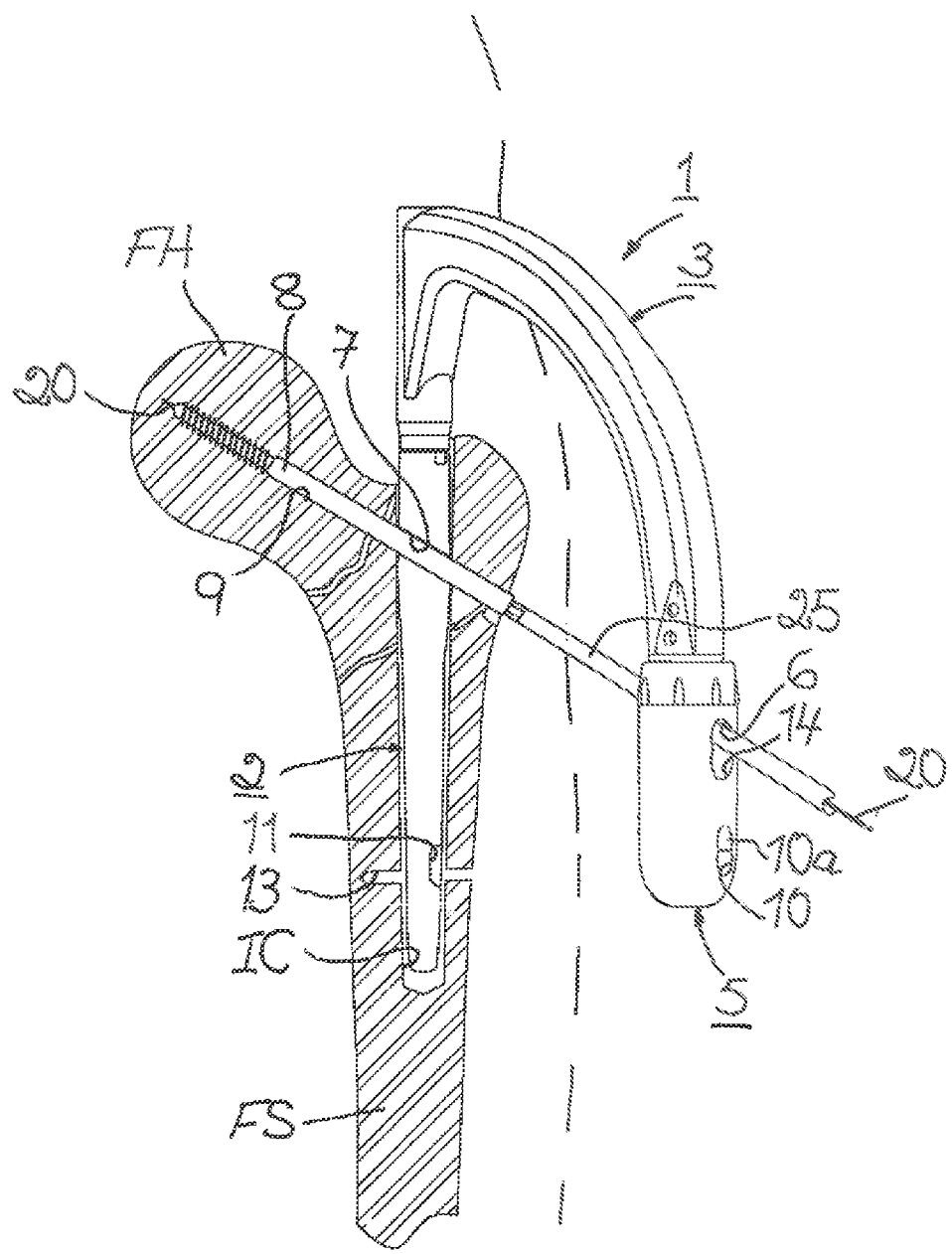
FIG. 11 is a schematic sectional view of the targeting device with the intramedullary cavity nail in position in the intramedullary canal of the femoral shaft of the fractured femur and during insertion of the femur neck screw.
Figure 12:
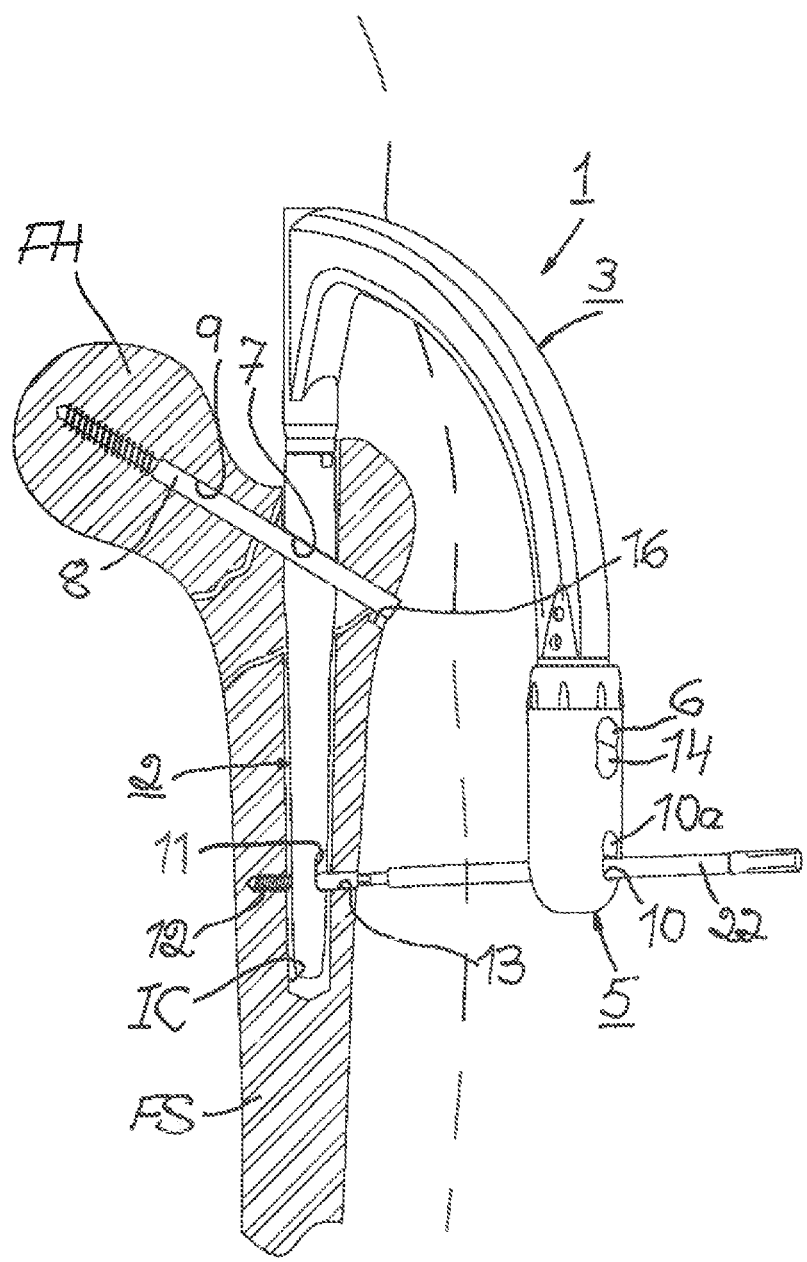
FIG. 12 is a schematic sectional view of the targeting device with the intramedullary cavity nail in position in the intramedullary canal of the femoral shaft of the fractured femur and during insertion of the diaphysis screw.

Finally, after removal of all working tools (drills, cutters etc.), the cavity nail 2 is fixed in the intramedullary canal IC of the femoral shaft FS by screwing or threading the femur neck screw 8 and the diaphysis screw 12 into the respective hole 9 and 13 respectively, therefor, as illustrated in FIGS. 11 and 12. This can be done manually, e.g. by means of a screw driver 25 as illustrated in FIG. 11, or by means of a power tool. Then, any guide sleeves and/or K-wires which have been used for guiding the screws 8, 12, are removed. As an alternative already mentioned above, the recess 16 can be provided first after fixing the cavity nail 2 by means of said femur neck screw 8 and said diaphysis screw 12.

A set screw (not illustrated) of any prior art type can be brought in engagement with the femur neck screw 8, which then is configured to fit with the set screw, for preventing relative displacement of the femur neck screw and the cavity nail 2 when no secondary compression therealong as defined above is desired, i.e. only uniaxial compression in the longitudinal direction of the femoral shaft FS and the cavity nail is permitted, unless the diaphysis screw 12 is situated in the proximal part of the oblong through-hole 11 in the cavity nail 2 and thereby prevents displacement of the femoral shaft and the cavity nail relative to each other.

Preferably, an end cap (not illustrated) is used to close the proximal part of the cavity nail 2 to prevent ingrowth therein of bone.

Preparations for closing the wounds can now be performed.

Fixing of the intramedullary cavity nail 2 can be carried through in many ways. Thus, the above-mentioned procedure can be varied in many ways and should not be regarded as the only possible operative technique. Certain steps can be eliminated or performed differently and/or in different order and other steps can be added.

It is obvious to a skilled person that the present invention can be modified and altered within the scope of the subsequent claims without departing from the idea and purpose of the invention. Thus, the targeting device may be made of any suitable metallic or plastic material and the components thereof may have any suitable size and shape in order to fulfil their respective function and fit with the various screws and the set of various instruments for fixing the cavity nail in the intramedullary canal of the femoral shaft of the fractured femur.

The invention claimed is:

1. A device for use in fixing an intramedullary cavity nail (2) for the treatment of unstable trochanteric femur fractures, comprising:
 a cavity nail (2) adapted to be inserted into an intramedullary canal (IC) of a femoral shaft (FS) of a fractured femur; and
 a targeting device (1) comprising
 a targeting arm (3) releasably connected to the cavity nail (2) at one free end of the targeting arm (3), and
 a targeting head (5) with targeting bores (6, 10, 14) at the other free end of the targeting arm (3);
 wherein at least one of the targeting bores (6) in the targeting head (5) is adapted to serve as a guide for providing a hole (9) for a femur neck screw (8) that is configured to extend through the femoral shaft (FS) and through an inclined proximal through-hole (7) in the cavity nail (2), the through hole (7) in the cavity nail (2) being configured to allow displacement of said cavity nail (2) relative to the femur neck screw (8) and prevent the cavity nail (2) from displacement relative to the femoral shaft (FS) in a longitudinal direction thereof,
 at least one of the targeting bores (10) in the targeting head (5) is adapted to serve as a guide for providing a hole (13) for a diaphysis screw (12) that is configured to extend into the femoral shaft (FS) and through an oblong distal through-hole (11) provided in the cavity nail (2), the oblong distal through-hole (11) of the cavity nail (2) being configured to permit displacement of the cavity nail (2) relative to the femoral shaft (FS) in the longitudinal direction thereof, and
 at least one of the targeting bores (14) in the targeting head (5) is adapted to serve as a guide for providing a recess (16) for the femur neck screw (8) in at least the lateral cortex of the femoral shaft (FS) and in close proximity to the hole (9) for the femoral neck screw (8) to form an oblong recess (16) therewith, wherein the targeting head (5) is connected to the targeting arm (3) and is adjustable in a longitudinal direction of the targeting head (5), and the at least one targeting bore (6) for use in providing the hole (9) for the femur neck screw (8) and the at least one targeting bore (14) for use in providing the recess (16) for the femur neck screw are made up of one and the same targeting bore (6, 14), thereby permitting a biaxial compression of the trochanteric femur fracture along the femur neck screw (8) and in the longitudinal direction of the femoral shaft (FS) or cavity nail (2) during secondary compression.

2. The device according to claim 1, wherein the at least one targeting bore (6, 14) for use as a guide in providing the recess (16) for the femur neck screw (8) is configured for receiving therein a working tool (15) for providing the recess (16).

3. The device according to claim 2, wherein the at least one targeting bore (6, 14) for use as a guide in providing the recess (16) for the femur neck screw (8) is configured to provide, by means of the working tool (15) received therein, the recess (16) with a length of 5-10 mm.

4. The device according to claim 3, wherein the at least one targeting bore (6, 14) for use as a guide in providing the recess (16) for the femur neck screw (8) is configured for receiving therein the working tool (15) with a diameter of 5-10 mm.

5. The device according to claim 4, wherein the working tool (15) has a diameter of 7 mm.

6. The device according to claim 3, wherein the recess (16) has a length of 7 mm.

7. The device according to claim 2, wherein the at least one targeting bore (6, 14) for use as a guide in providing the recess (16) for the femur neck screw (8) is configured to provide, by means of the working tool (15) received therein, the recess (16) with a diameter of 5-10 mm.

8. The device according to claim 7, wherein the recess (16) has a diameter of 7 mm.

9. The device according to claim 1, wherein the at least one targeting bore (6, 14) for use as a guide in providing the recess (16) for the femur neck screw (8) or a guide (24) for a working tool (15) received in said targeting bore (6, 14) is configured with a stop means (17) for engagement by a mating stop means (18) on the working tool for limiting the depth of the recess (16) provided in the lateral cortex of the femoral shaft (FS).

10. The device according to claim 1, wherein the at least one targeting bore (10) for use as a guide in providing the hole (13) for the diaphysis screw (12) is alignable with the oblong distal through-hole (11) for said diaphysis screw in the cavity nail (2) such that relative displacement of the cavity nail (2) is permitted in the longitudinal direction of the femoral shaft (FS).

11. The device according to claim 10,
wherein the at least one targeting bore (10) for use as a guide in providing the hole (13) for the diaphysis screw (12) is alignable with the oblong distal through-hole (11) for said diaphysis screw in the cavity nail (2) such that relative displacement of the cavity nail (2) is not permitted in the longitudinal direction of the femoral shaft (FS).

12. The device according to claim 10, wherein the targeting head (5) is configured with two targeting bores (10, 10a) for use as guides in providing the hole (13) for the diaphysis screw (12),
wherein one of said targeting bores (10) is alignable with the oblong distal through-hole (11) for said diaphysis screw (12) in the cavity nail (2) such that relative displacement of the cavity nail (2) is permitted in the longitudinal direction of the femoral shaft (FS), and
wherein the other of said targeting bores (10a) is alignable with the oblong distal through-hole (11) for said diaphysis screw (12) in the cavity nail (2) such that relative displacement of the cavity nail is not permitted in the longitudinal direction of the femoral shaft (FS).

13. The device according to claim 12, wherein the two targeting bores (10, 10a) for use as guides in providing the hole (13) for the diaphysis screw (12) are provided in the targeting head (5) such that they are totally or partly separated from each other.

14. The device according to claim 13, wherein the two targeting bores (10, 10a) for use as guides in providing the hole (13) for the diaphysis screw (12) are provided in the targeting head (5) such that the upper peripheral part of one of said targeting bores (10) intersects with the lower peripheral part of the other of said targeting bores (10a).

15. The device according to claim 13, wherein the two targeting bores (10, 10a) for use as guides in providing the hole (13) for the diaphysis screw (12) are provided in the targeting head (5) at a distance from each other in the same longitudinal plane through the targeting head and in parallel with each other.

16. The device according to claim 13, wherein the targeting head (5) is connected to the targeting arm (3) and is rotatable about a longitudinal axis of the targeting head (5), and
wherein the two targeting bores (10, 10a) for use as guides in providing the hole (13) for the diaphysis screw (12) are provided in the targeting head (5) at a distance from each other, in two different longitudinal planes through the targeting head,
axes of the two targeting bores (10, 10a) for use as guides in providing the hole (13) for the diaphysis screw (12) extending through the targeting head (5) are at the same angle relative to the longitudinal axis of the targeting head.

* * * * *